(12) United States Patent
Riedl et al.

(10) Patent No.: US 12,371,441 B2
(45) Date of Patent: Jul. 29, 2025

(54) SIDEROPHORE CEPHALOSPORIN CONJUGATES AND USES THEREOF

(71) Applicant: ARIVA MED GMBH, Vienna (AT)

(72) Inventors: Rosemarie Riedl, Vienna (AT); Susanne Paukner, Vienna (AT); Wolfgang Wicha, Bruck an der Leitha (AT); Josef Wieser, Polling in Tirol (AT); Klaus Thirring, Vienna (AT); Hermann Kollmann, Linz (AT)

(73) Assignee: ARIVA MED GMBH, Vienna (AT)

( * ) Notice: Subject to any disclaimer, the term of this patent is extended or adjusted under 35 U.S.C. 154(b) by 743 days.

(21) Appl. No.: 17/640,506

(22) PCT Filed: Sep. 4, 2020

(86) PCT No.: PCT/EP2020/074754
§ 371 (c)(1),
(2) Date: Mar. 4, 2022

(87) PCT Pub. No.: WO2021/043973
PCT Pub. Date: Mar. 11, 2021

(65) Prior Publication Data
US 2022/0332728 A1    Oct. 20, 2022

(30) Foreign Application Priority Data
Sep. 6, 2019 (EP) .................................. 19195809

(51) Int. Cl.
| C07D 501/46 | (2006.01) |
| A61K 47/55 | (2017.01) |
| A61P 31/04 | (2006.01) |

(52) U.S. Cl.
CPC ............ *C07D 501/46* (2013.01); *A61K 47/55* (2017.08); *A61P 31/04* (2018.01)

(58) Field of Classification Search
CPC .................................................. C07D 501/46
See application file for complete search history.

(56) References Cited

U.S. PATENT DOCUMENTS

| 4,500,526 | A | 2/1985 | Imae et al. |
| 5,081,248 | A | 1/1992 | Zama et al. |
| 5,143,910 | A | 9/1992 | Onoue et al. |
| 5,856,474 | A | 1/1999 | Ascher et al. |
| 6,531,465 | B1 | 3/2003 | Ascher et al. |
| 9,085,589 | B2 | 7/2015 | Kusano et al. |
| 9,238,657 | B2 | 1/2016 | Nishitani et al. |
| 9,334,289 | B2 | 5/2016 | Nishitani et al. |
| 9,630,977 | B2 | 4/2017 | Cho et al. |
| 2011/0190254 | A1 | 8/2011 | Nishitani et al. |
| 2013/0096299 | A1 | 4/2013 | Kusano et al. |
| 2013/0178455 | A1 | 7/2013 | Cho et al. |
| 2014/0088302 | A1 | 3/2014 | Nishitani et al. |

FOREIGN PATENT DOCUMENTS

| EP | 0 416 410 A1 | 3/1991 |
| EP | 0 430 286 A2 | 6/1991 |
| EP | 2 341 053 A1 | 7/2011 |
| WO | 95/29182 A1 | 11/1995 |
| WO | 96/35692 A1 | 11/1996 |
| WO | 98/43981 A1 | 10/1998 |
| WO | 2010/050468 A1 | 5/2010 |
| WO | 2011/136268 A1 | 11/2011 |
| WO | 2012/134184 A2 | 10/2012 |
| WO | 2012/147773 A1 | 11/2012 |

OTHER PUBLICATIONS

Weinstein, M.P., et al., "Methods for Dilution Antimicrobial Susceptibility Tests for Bacteria That Grow Aerobically," Clinical and Laboratory Standards Institute, M07, 11th Edition (Jan. 2018).
Weinstein, M.P., et al., "Performance Standards for Antimicrovial Susceptibility Testing," Clinical and Laboratory Standards Institute, M1000, 29th Edition (Jan. 2019).
Ji, C., et al., "Exploiting bacterial iron acquisition: siderophore conjugates," Future Med. Chem., vol. 4, No. 3, pp. 297-313 (2012).
Schwyn B., et al., "Universal Chemical Assay for the Detection and Determination of Siderophores," Analytical Biochemistry 160, pp. 47-56 (1987).
Luscher, A., et al., "TonB-Dependent Receptor Repertoire of Pseudomonas aeruginosa for Uptake of Siderophore-Drug Conjugates," Antimicrobial Agents and Chemotherapy, vol. 62, No. 6, pp. 1-11 (2018).

*Primary Examiner* — Susanna Moore
(74) *Attorney, Agent, or Firm* — Venable LLP

(57) ABSTRACT

A compound of compound according to formula (I):

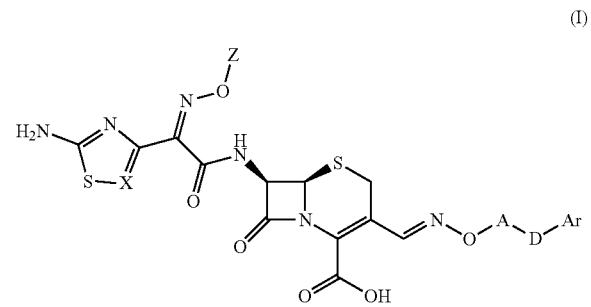

wherein X is selected from the group consisting of CH, CCl and N, Z is selected from the group consisting of $CH_2COOH$, $CH(CH_3)COOH$, $C(CH_3)_2COOH$ and $CH_2F$, D is a single bond connecting A and Ar or selected from the group consisting of CO, NHCO and $N(C_{0-6})$alkyl-CO, A is selected from the group consisting of a $(C_{1-6})$alkanediyl and a $(C_{3-6})$cycloalkanediyl or, if D is $N(C_0)$alkyl-CO, A forms a 4- to 7-membered aliphatic heterocyclic ring with the nitrogen atom of $N(C_0)$alkyl-CO in D, and Ar is a 6-membered aromatic ring with a first hydroxyl group in para-position to D, a second hydroxyl group in meta-position to D, and with at least one electron-withdrawing element and uses thereof.

30 Claims, No Drawings

SIDEROPHORE CEPHALOSPORIN CONJUGATES AND USES THEREOF

The present application is a national-stage entry under 35 U.S.C. § 371 of International Patent Application No. PCT/EP2020/074754, published as WO 2021/043973 A1, filed Sep. 4, 2020, which claims priority to EP 19195809.9, filed Sep. 6, 2019, the entire disclosure of each of which is hereby incorporated by reference.

BACKGROUND OF THE INVENTION

Field of the Invention

The present invention relates to organic compounds, namely siderophore cephalosporin conjugates and uses thereof.

Cephalosporins are a class of 3-lactam antibiotics with a common core structure, i.e. the cephem ring system 8-oxo-5-thia-1-azabicyclo[4.2.0]oct-2-ene-2-carboxylate. The bacterial spectrum, i.e. the cephalosporin's bactericidal activity against different bacteria, varies depending on the substitution pattern. Cephalosporin compounds comprising an CH=N moiety in the side chain in position 3 of the cephem ring are e.g. described in WO96/35692, with oxime type CH=N—O compounds exemplified in Example 3, 4 and 6 therein.

Siderophores are iron chelation compounds and siderophore drug conjugates utilize the iron uptake mechanism in bacteria. Some examples of siderophore drug conjugates are e.g. summarized in Ji, C. et al, *Future Med. Chem.* (2012) 4(3), 297-313.

Siderophore conjugate cephalosporins are e.g. described in WO2010/050468, WO2011/136268, WO2012/134184 and WO2012/147773 covering derivatives with an alkyl or alkenyl together with a quaternary ammonium group at the side chain in position 3 of the cephem ring. In e.g. WO2010/050468 cefiderocol is exemplified, a catechol type siderophore cephalosporin conjugate representing the most advanced siderophore drug conjugate, currently being in pre-registration stage for the potential intravenous treatment of multidrug resistant (MDR) Gram-negative bacterial infections.

The present invention provides a compound according to formula (I):

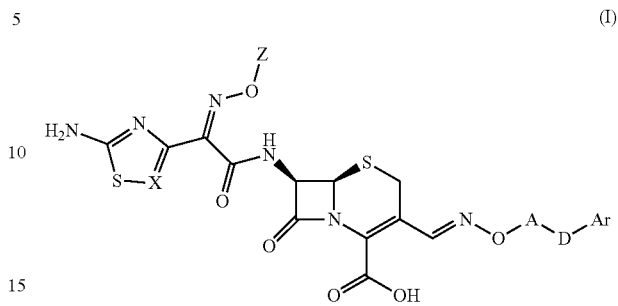

wherein

X is selected from the group consisting of CH, CCl and N,

Z is selected from the group consisting of CH2COOH, CH(CH3)COOH, C(CH3)2COOH, and CH2F, D is a single bond connecting A and Ar or selected from the group consisting of CO, NHCO and N(C0-6)alkyl-CO, A is selected from the group consisting of
- a (C1-6)alkanediyl and
- a (C3-6)cycloalkanediyl or if D is N(CO)alkyl-CO, A forms a 4- to 7-membered aliphatic heterocyclic ring with the nitrogen atom of N(CO)alkyl-CO in D, and Ar is a 6-membered aromatic ring with a first hydroxyl group in para-position to D, a second hydroxyl group in meta-position to D and with at least one electron-withdrawing element.

In the compounds according to the present invention, a siderophore group (Ar) is linked to the cephalosporin core by a linkage including an oxime ether at position 3 of the cephem ring. The resulting siderophore conjugate cephalosporins of oxime type have not been described before. The

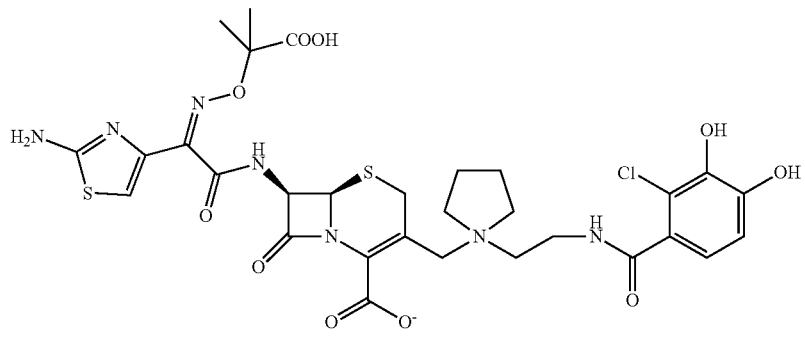

(cefiderocol)

Strong iron chelating properties are important for the siderophore drug conjugates to be able to compete with natural siderophores excreted by microorganisms.

inventors surprisingly found that the siderophore conjugate cephalosporins of oxime type, i.e. compounds according to formula (I), have an interesting anti-bacterial activity com bined with unexpectedly strong iron-chelating properties. The oxime linkage of the siderophore group (Ar) is involved in the surprisingly strong iron-chelating properties. Example 4, which differs to the compound cefiderocol mainly in the linker, shows an iron-chelating activity being an order of magnitude stronger than the one measured for cefiderocol (see table 1 below).

In a compound according to formula (I), Ar is considered to be mainly responsible for the compound's iron-chelating properties. Ar is a 6-membered aromatic ring with two hydroxyl groups. Both hydroxyl-groups are in ortho-substitution to each other (catechol type), which is known to allow complexing of an iron atom (i.e. iron-chelating). The first hydroxyl group occupies the position opposite to the position which is linked to the rest of the compound (i.e., para-position). The second hydroxyl group occupies a position at a carbon atom adjacent to the carbon atom to which the first hydroxyl group is bound (i.e., meta-position to the position, which is linked to the rest of the compound).

In a compound according to the present invention, the siderophore group Ar further has at least one electron-withdrawing element.

Electron withdrawing is a concept known in organic chemistry and describes polarization or electrostatic forces with respect to a reaction center or in the present case to the electron system in the aromatic ring. Electron-withdrawing elements may be e.g. electron withdrawing substituents at the aromatic ring. If D is selected from CO, NHCO and $N(C_{0-6})$alkyl-CO, then the aromatic ring Ar is substituted with a carbonyl group, which is known to have an electron-withdrawing effect. However, according to the present invention, Ar has at least one additional electron-withdrawing element.

The further electron-withdrawing element may be a substituent positioned at any free position of the aromatic ring. Electron-withdrawing substituents include e.g. halogen, nitrile, carbonyl (in particular C1-C6 carbonyl, such as formyl, acetyl) or halogenated alkoxyl.

In a preferred embodiment, the electron-withdrawing substituent is a substituent selected from the group consisting of F, Cl and $OCF_3$. In particular, the electron-withdrawing substituent is a substituent at a free position of the aromatic ring, preferably, in ortho-position to D.

Alternatively or additionally, the electron-withdrawing element may be a heteroatom in the aromatic ring Ar.

In a preferred embodiment, the electron-withdrawing element is a nitrogen atom or a substituted nitrogen atom in the aromatic ring Ar. Thus, the resulting aromatic ring Ar is a pyridine-based aromatic ring. For example the aromatic ring may be selected from the group consisting of a pyridine, an N-(C1.6)alkyl-pyridinium, and a pyridine-N-oxide. Preferably, the pyridine-based aromatic ring is substituted with the two hydroxy groups at position 3 and 4 (or 4 and 5) with respect to the nitrogen atom and linked to D (or the rest of the molecule) at position 2 (or 6) with respect to the nitrogen atom. Exemplarily, Ar is selected from the group consisting of a 3,4-dihydroxy-2-pyridinyl, 4,5-dihydroxy-2-pyridinyl, 3,4-dihydroxy-1-($C_1$-$C_6$)alkyl-2-pyridiniumyl, 4,5-dihydroxy-1-(C1-$C_6$)alkyl-2-pyridiniumyl, 1,3-dihydroxy-4-oxo-2-pyridyl and 1,5-dihydroxy-4-oxo-2-pyridyl, preferably 4,5-dihydroxy-2-pyridinyl, 4,5-dihydroxy-1-($C_1$-$C_6$) alkyl-2-pyridiniumyl, 1,5-dihydroxy-4-oxo-2-pyridyl.

In a further preferred embodiment, the compound according to the invention is a compound according to formula (II)

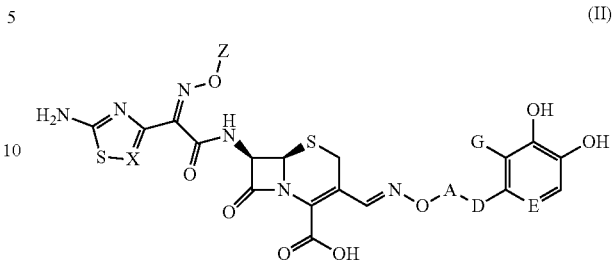

(II)

wherein X, Z, D, and A are as defined as indicated above and
wherein
E is selected from the group consisting of CH, N, N+—CH3, and N+—O—,
G is H or an electron-withdrawing substituent,
with the provision that if E is CH, D is selected from the group consisting of CO, NHCO and $N(C_{0-6})$alkyl-CO and G is an electron-withdrawing substituent.

In these embodiments, it is ensured that if E is CH, i.e. if the aromatic ring Ar is a phenyl-based ring, then the substituent G as well as D are selected to imply electron withdrawing. This means that if E is CH, then G is an electron withdrawing substituent and D includes a carbonyl function.

In this case, preferably, G is selected from the group consisting of F, Cl and $OCF_3$.

In one embodiment, the linker element D is selected from the group consisting of CO, NHCO and $N(C_{0-6})$alkyl-CO, more preferably from the group consisting of NHCO and $N(C_{0-6})$alkyl-CO, and in particular NHCO and $N(C_0)$alkyl-CO. If D is $N(C_0)$alkyl-CO, A forms a 4- to 7-membered aliphatic heterocyclic ring with the nitrogen atom of $N(C_0)$alkyl-CO in D. In this case, A forms both substituents for the nitrogen and the further alkyl substituent is absent, i.e. defined as $(C_0)$alkyl.

The linker element A (together with D) affects the geometrical arrangement (e.g. distance, orientation) of Ar with respect to the cephem ring. Generally, A is selected independent from D. However, in some embodiments, the definition of A relates to D. Based on preliminary data, it is believed that it is beneficial, in particular for the iron chelating activity, that the O of the oxime group and the closest atom of Ar are separated by at least one atom (such as in Example 1), but preferably not more than six atoms, e.g. five atoms. A distance can be described by the number of covalent bonds in the shortest linking path within a molecule (or within a part of a molecule). This is a very simplified representation neglecting conformational/three dimensional aspects, but allows to define some preferences for the linker according to the present invention. The person of ordinary skill in the art will appreciate that covalent bonds including heteroatoms, covalent (C—C) bonds involving C atoms with sp2 hybridization as well as cyclic (C—C) bonds (due to geometrical constraints within a ring system) are shorter than acyclic covalent (C—C) single bond.

Herein, a shortest linking path in A is defined by the number of bonds extending between the O of the oxime group and D, excluding the bond to the O of the oxime group (i.e. excluding the bond O-A in formula (I) or (II)) and excluding the bond to D or the single bond of D (i.e. excluding the bond A-D in formula (I) or (II)). As follows from the term "shortest", in case of furcated or cyclic linkers, the path with the lowest number of bonds is to be considered.

In one embodiment, A is selected such that the shortest linking path in A is shorter than or equal to 3 covalent (C—C) single bonds, in particular shorter than 3 acyclic covalent (C—C) single bond, and preferably shorter than or equal to 2 covalent (C—C) single bonds, in particular shorter than 2 acyclic covalent (C—C) single bonds.

In a preferred embodiment, the shortest linking path in A extends over no single (C—C) bond, one cyclic or acyclic (C—C) single bond, or two cyclic covalent (C—C) bonds Accordingly, in a preferred embodiment A is selected from the group consisting of methanediyl, ethane-1,2-diyl, propane-1,3-diyl, propane-1,2-diyl, cyclobutane-1,3-diyl, cyclopentane-1,3-diyl, cyclohexane-1,3-diyl, azetidine-1,3-diyl, pyrrolidine-1,3-diyl and piperidine-1,3-diyl, wherein in azetidine-1,3-diyl, pyrrolidine-1,3-diyl and piperidine-1,3-diyl D is $N(C_0)$alkyl-CO and the nitrogen atom of $N(C_0)$alkyl-CO in D is the nitrogen in the heterocyclic ring, preferably selected from the group consisting of methanediyl, ethane-1,2-diyl, cyclobutane-1,3-diyl, and pyrrolidine-1,3-diyl with D being $N(C_0)$alkyl-CO and the nitrogen atom of $N(C_0)$alkyl-CO in D being the nitrogen in the pyrrolidine ring.

In a further embodiment, the compound according to the invention is a compound according to formula (II),
wherein X and Z are defined as indicated above and
D is NHCO or $N(C_{0-6})$alkyl-CO,
A is
a $(C_{1-6})$alkanediyl, preferably a $(C_{1-4})$alkanediyl, such as in particular the $(C_2)$alkanediyl ethane-1,2-diyl,
a $(C_{3-6})$cycloalkanediyl, preferably $(C_{4-5})$cycloalkanediyl, such as in particular the $(C_4)$cycloalkanediyl cyclobutane-1,3-diyl, or
A forms a 4- to 7-membered aliphatic heterocyclic ring with the nitrogen atom of $N(C_0)$alkyl-CO in D, preferably a 5-membered aliphatic heterocyclic ring, such as in particular the 5-membered heterocyclic ring pyrrolidine-1,3-diyl with the nitrogen atom of $N(C_0)$alkyl-CO in D being the nitrogen in the pyrrolidine,
E is CH,
G is $C_1$.

Alternatively, if E is N, $N^+$—$CH_3$, and $N^+$—O, i.e. if the aromatic ring Ar is a pyridinyl-based ring, then no such requirements as to G and D are implied. The heteroatom N is the electron withdrawing element in Ar. Thus, G may also be hydrogen and/or D may be a single bond (i.e. D is not present as individual moiety).

Preferably, in this case, the compound according to the invention is a compound according to formula (II),
wherein X and Z are defined as indicated above and
wherein D is a single bond
A is
a $(C_{1-6})$alkanediyl, preferably a $(C_{1-4})$alkanediyl, such as methanediyl,
a $(C_{3-6})$cycloalkanediyl or
E is $N^+$—$O^-$,
G is H.

In another embodiment, it is preferred that -A-D-Ar in formula (I) is selected from the group consisting of

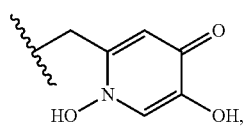

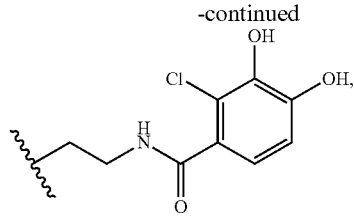

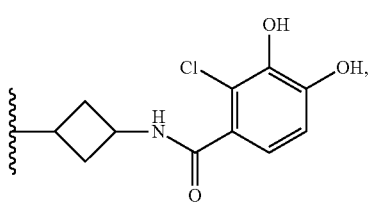

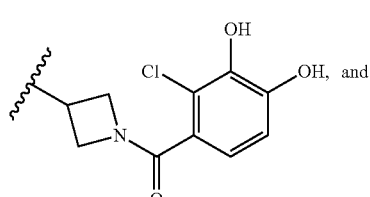

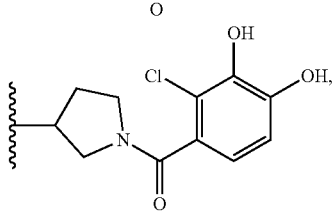

preferably from the group consisting of

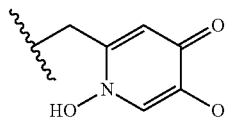

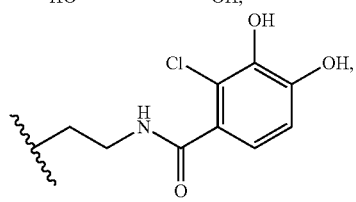

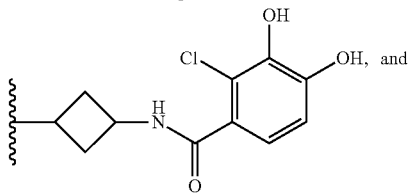

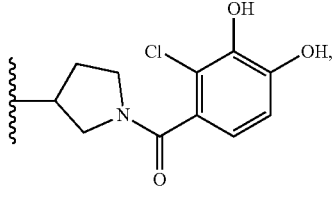

more preferably from the group consisting of

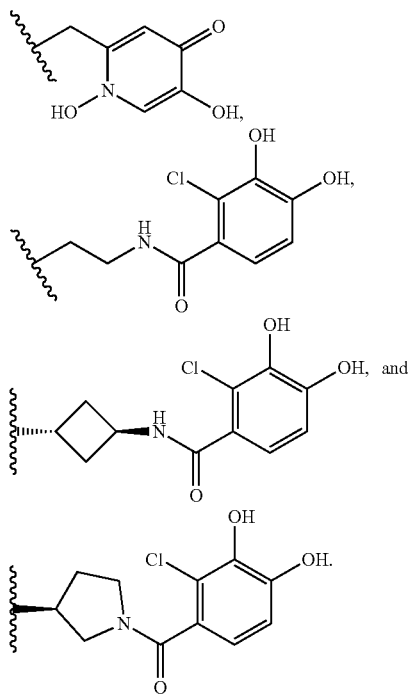

The compound of the invention includes a thiazole ring (X is CH or X is CCl) or a 1,3,4-thiadiazole (X is N).

In a preferred embodiment, X is CH or N.

The oxime in the substitution at the 7-position is O-substituted with a substituted alkyl Z, which is selected from the group consisting of $CH_2COOH$, $CH(CH_3)COOH$, $C(CH_3)_2COOH$ and $CH_2F$.

In a preferred embodiment, Z is $C(CH_3)_2COOH$ or $CH_2F$.

In another aspect, the present invention provides a composition comprising a compound according to the invention in association with at least one pharmaceutical excipient.

In one embodiment, the composition optionally comprises further at least one pharmaceutical active agent.

In another aspect, the present invention provides the compound or composition according to the invention for use as medicine.

The compound or the composition according to the invention may be used in a method of treatment or prevention of a disease, wherein the compound or the composition comprising the compound according to the invention is applied to a subject in need thereof.

It was found that the compounds according to the invention have a bactericidal activity. Thus, they are suitable for treatment and prevention of infectious diseases.

Therefore, in one embodiment, the present invention provides the compound or the composition according to the invention for use in treatment and prevention of an infectious disease mediated by microbes or bacteria, preferably Gram-negative bacteria.

In a preferred embodiment, the infectious disease is selected from the group consisting of a respiratory tract infection of the upper and/or lower respiratory tract, wherein a respiratory tract infection includes cystic fibrosis and bronchiectasis,
an urinary tract infection,
an intraabdominal infection,
a systemic infection,
a prosthetic joint infection,
a gastrointestinal infection, and
an infection of skin and/or soft tissue.

In another embodiment, the infectious disease is mediated by a bacteria selected from the group consisting of *Escherichia coli, Salmonella typhimurium, Citrobacter freundii, Klebsiella pneumoniae, Enterobacter cloacae, Enterobacter aerogenes, Moraxella catarrhalis, Proteus mirabilis, Proteus vulgaris, Providencia stuartii, Serratia marcescens, Acinetobacter baumannii, Acinetobacter lwoffi, Pseudomonas aeruginosa, Haemophilus influenzae, Burkholderia cepacia, Burkolderia cenocepatia, Burkholderia vietnamensis, Streptococcus* spp., and *Streptococcus pneumoniae*, preferably selected from the group consisting of *Escherichia coli, Klebsiella pneumoniae, Acinetobacter baumannii, Pseudomonas aeruginosa*, and *Burkholderia cepacia*.

In a further aspect, the present invention provides a method of treating an infectious disease in a subject in need thereof, comprising administering an effective amount of a compound according to formula (I) to the subject, wherein in the compound according to formula (I) X, Z, A, D and Ar are defined as indicated above.

In one embodiment, the compound is administered in the form of a pharmaceutical composition. Treating includes treatment and prophylaxis. For antimicrobial and cystic fibrosis treatment, the appropriate dosage (effective amount) will, of course, vary depending upon, for example, the chemical nature and the pharmacokinetic data of a compound of the present invention employed, the individual host, the mode of administration, and the nature and severity of the disease(s) being treated. However, in general, for satisfactory results in large mammals, for example humans, and indicated daily dosage is in the range of from about 0.5 mg to 3 g of a compound of the present invention conveniently administered for example in divided doses up to four times a day.

Description of Related Art

The definition of a $(C_{X-Y})$group in a compound according to formula (I) or (II) includes any group with X to Y carbon atoms. For example, a (C1-5)alkyl includes for example methyl, ethyl, propyl, prop-2-yl, butyl, but-2-yl, trimethylmethyl, 2-methylprop-1-yl, pentyl, pent-2-yl, pent-3-yl, 2-methylbutyl, 3-methylbutyl, 3-methylbut-2-yl. In analogy, also a $(C_1-C_6)$alkyl or a $(C_{1-6})$alkanediyl includes linear and branched alkane groups.

Any group defined as part of the compound according to the invention may be unsubstituted or substituted, e.g. one or more fold.

$(C_{1-6})$alkyl, $(C_{1-6})$alkanediyl, cycloalkyl, $(C_{3-6})$cycloalkanediyl, 4- to 7-membered aliphatic heterocyclic ring, and 6-membered aromatic ring include unsubstituted or substituted $(C_{1-6})$alkyl, $(C_{1-6})$alkanediyl, cycloalkyl, $(C_{3-6})$cycloalkanediyl, 4- to 7-membered aliphatic heterocyclic ring, and 6-membered aromatic ring, respectively. These groups may be substituted, e.g., by groups which are conventional in organic chemistry. Substituents include for example $(C_1-C_6)$alkyl, $(C_2-C_6)$alkenyl, $(C_1-C_6)$alkoxy, hydroxy, oxo, carboxyl, $(C_1-C_6)$alkylcarbonyl, amido, ureido, guanidino, thioureido, amino, halogen.

The groups A and D (if D is not a single bond) both are linking groups with two free valences for forming the bond to other parts of the compound. If not indicated otherwise, the linking groups A or D is/are oriented in formula (I) or (II) as written from left to right. For example, if D is NHCO in formula (I) the nitrogen atom of the amide is linked to A and the carbon atom linked to Ar.

A compound according to the invention has two oxime ether functionalities, also referred to as oxy-imine function. For these functionalities different stereochemical orientations are possible based on the E/Z configuration at the double bond to the nitrogen atom (C=N bond). It is to be understood, that the drawing of the orientation in a formula should not exclude alternative configurations. Thus, in a compound according to formula (I) or (II) all configurational isomer should be understood to be covered if the stereochemistry is not explicitly indicated (i.e. as in the case of the chiral carbon atoms of at the cephem ring). Especially, for both oxime functionalities, independently from each other, both configurations are included in formula (I) or (II), thus also the respective four diastereomer forms are covered. However, it is preferred that each of the oxime functionalities independently from each other are in the configuration as visualized by the drawing of formula (1) or (II), more preferably both are in the configuration as visualized by the drawing of formula (I) or (II).

A pyridine-N-oxide, pyridinone or pyridinium may exist in tautomeric forms:

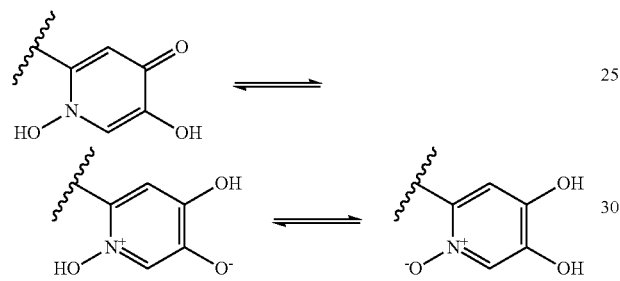

The present invention includes all tautomeric forms independently of the tautomer selected for drawing of the respective formula or the nomenclature.

A compound of the present invention includes a compound in any form, e.g. in free form/inner salt/zwitterionic form, in the form of a salt, in the form of or a solvate, or a salt and a solvate. The salts include preferably pharmaceutically acceptable salts, although any salt is included, e.g. for preparation/isolation/purification purposes.

Methods for the preparation of compounds of the present invention are known or may be prepared according, e.g. analogously, to a method as conventional or as specified in the synthetic Scheme 1 below:

Scheme 1

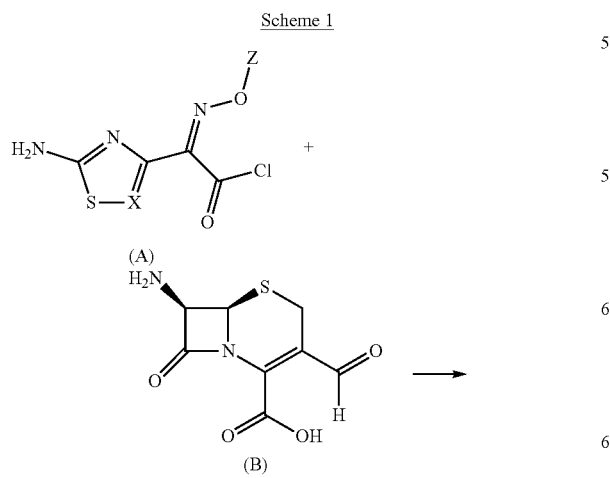

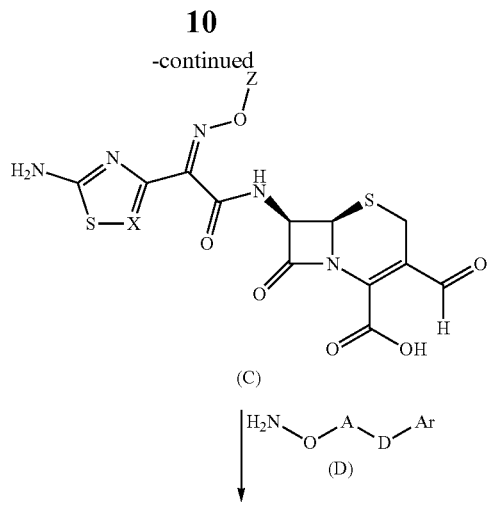

(C)

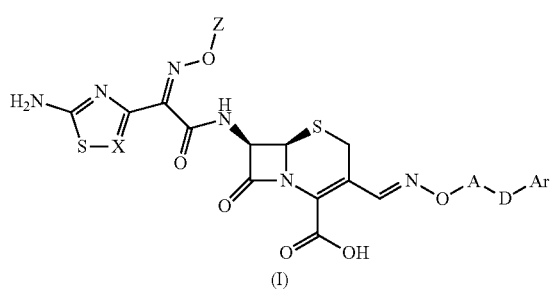

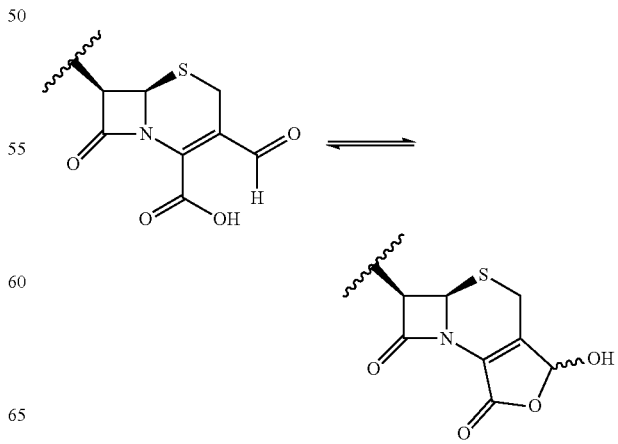

In compounds of formula (I), formula (A) and formula (D), X, Z, A, D, and Ar are as defined above.

Intermediates or starting materials (A), (B) and (D), optionally in protected form or in the form of a salt, or both, in the preparation of a compound of the present invention are known or may be prepared according, e.g. analogously, to a method as conventional.

The intermediate or starting material of formulae (B) and (C) contain an aldehyde, which together with the proximal carboxylic acid may exist as hemi-acylal:

A compound of the present invention may be used for (or applied in a method for) treatment or prophylaxis (i.e. prevention), wherein the compound of the present invention is applied to a subject, i.e. administered.

A compound of the present invention may be administered by any conventional route, for example enterally, e.g. including nasal, buccal, oral administration; parenterally, e.g. including intravenous, intramuscular, subcutaneous administration; or topically, e.g. including inhalation, epicutaneous, intranasal, intratracheal, intraotic, ophthalmic administration, e.g. in form of coated or uncoated tablets, capsules, injectable solutions or suspensions, e.g. in the form of ampoules, vials, in the form of creams, gels, pastes, inhalation liquid, inhaler powder, sprays, foams, tinctures, or drops.

Preferably, a compound according to the invention is not administered in pure form, but is formulated in a composition.

Thus, in another aspect the present invention provides a pharmaceutical composition comprising a compound of the present invention association with at least one pharmaceutical excipient, e.g. carrier or diluent. Therein, the compound according to the invention may be in free form or in the form of a pharmaceutically acceptable salt and/or in the form of a solvate.

Depending on the route for administration, the composition is formulated according to the state of the art of pharmaceutical galenics. The person skilled in the art can select the at least one pharmaceutical excipient from known excipients, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers A compound of the present invention may be used for (or applied in a method for) treatment or prophylaxis either alone or in combination with one or more other pharmaceutically active agents. Such other pharmaceutically active agents include e.g. beta-lactamase inhibitors, potentiators and other antibiotics, and, if a compound of the present invention is used in the treatment of cystic fibrosis, other pharmaceutically active agents include furthermore agents, which are conventionally used in the treatment of cystic fibrosis.

The other pharmaceutically active agent may be provided in the composition comprising the compound according to the invention or the other pharmaceutically active agent may be administered separately.

The use and methods of the present invention primarily relate to the treatment and prevention in human subjects, but can also be employed for the treatment and prevention in other mammalian subjects, i.e. animals and pets such as fowl, pigs, calves, dogs, cats, i.e. for veterinary purposes as well as for diluting fluids for artificial insemination and for egg-dipping techniques.

A compound of the present invention may be used for (or applied in a method for) treatment or prevention of infectious diseases. The infectious disease may be diagnosed by a person skilled in the art, who associates the symptoms of a subject with an infection by microbes or bacteria or the infectious disease may be diagnosed by detecting microbes or bacteria in the subject or a sample taken from the subject.

The compounds according the present invention exhibit pharmacological activity and are therefore useful as pharmaceuticals. For example, the compounds of the present invention show antibacterial activity against Gram-negative bacteria, such as e.g. *Escherichia coli, Salmonella typhimurium, Citrobacter freundii, Klebsiella pneumoniae, Enterobacter cloacae, Enterobacter aerogenes, Moraxella catarrhalis, Proteus mirabilis, Proteus vulgaris, Providencia stuartii, Serratia marcescens, Acinetobacter baumannii, Acinetobacter lwoffi, Pseudomonas aeruginosa, Haemophilus influenzae, Burkholderia cepacia, Burkolderia cenocepatia, Burkholderia vietnamensis*, and Gram-positive bacteria, such as e.g.

*Streptococcus* spp. and *Streptococcus pneumoniae*.

An infectious disease mediated by Gram-negative bacteria may be mediated for example by bacteria selected from the group consisting of *Escherichia coli, Salmonella typhimurium, Citrobacter freundii, Klebsiella pneumoniae, Enterobacter cloacae, Enterobacter aerogenes, Moraxella catarrhalis, Proteus mirabilis, Proteus vulgaris, Providencia stuartii, Serratia marcescens, Acinetobacter baumannii, Acinetobacter lwoffi, Pseudomonas aeruginosa, Haemophilus influenzae, Burkholderia cepacia, Burkolderia cenocepatia*, and *Burkholderia vietnamensis*.

Compounds according to the present invention are therefore suitable for the treatment and prevention of diseases, which are mediated by microbes, e.g. by bacteria. Based on the antibacterial activity against gram-positive and gram-negative bacteria, a compound according to the present invention is suitable for treatment and prevention of an infection disease. Diseases, which may be treated with a compound according to the invention comprise e.g. upper and lower respiratory tract infections, including cystic fibrosis and bronchiectasis, as well as urinary tract infections, intraabdominal infections, systemic infections, prosthetic joint infections, gastrointestinal infections, and soft tissue infections.

The in vitro activity against bacteria was determined by standard broth microdilution according to the Clinical and Laboratory Standards Institute CLSI document (Performance Standards for Antimicrobial Susceptibility Testing) M100Ed29E (2019) and (Methods for Dilution Antimicrobial Susceptibility Test for Bacteria That Grow Aerobically) M07Ed11 (2018). The data were obtained using cation-adjusted Mueller Hinton broth medium (CAMHB), and additionally iron-depleted CAMHB medium (ID-CAMHB) for compounds with iron-chelating activity. Results for Examples 1 to 8 and comparative compounds are summarized in Table 1.

The iron-chelating property was determined by the chromeazurol assay according to Schwyn B., et al, Universal Chemical Assay for the Detection and Determination of Siderophores, 1987. Analytical Biochemistry 160: 47-56. The assay uses the affinity of chrome azurol S/iron(III)/hexadecyltrimethylamimonium bromide for iron(III). When a strong chelator removes the iron from this dye, its color turns from blue to orange and the absorbance measured at 630 nm is indicative for the chelating properties of a siderophore. Results for Examples 1 to 8 and comparative compounds are summarized in Table 1.

Accordingly, in one embodiment, the compound according to the invention has an iron-chelating activity defined by an IC50 of ≤40 µM, preferably <20 µM, wherein the iron-chelating activity is determined by a chromeazurol assay.

TABLE 1

| Species Strain | MIC in CAMHB medium (MIC in ID-CAMHB medium) [µg/mL] | | | | | Chrome-azurol Assay (CI95 LL-UL) IC$_{50}$ [µM] |
|---|---|---|---|---|---|---|
| | EC ATCC 25922 | KP ATCC 43816 | AB ATCC 15473 | PA ATCC 27853 | BC CF and non-CF isolates, n = 5 | |
| Ceftazidime | 0.12 | 0.12 | 4 | 2 | 4-16 | >100 |
| Ceftolozane | 0.25 | 0.25 | 2 | 0.5 | 2-8 | >100 |
| Cefiderocol | 0.25 (0.25) | 2 (0.5) | 0.25 (0.12) | 1 (0.5) | ≤0.03 (≤0.03) | 68.9 (46.1-103) |
| Example 1 | 0.12 (0.25) | ≤0.03 (0.25) | 2 (0.5) | 1 (0.25) | ≤0.03-0.06 (≤0.03-0.12) | 7.18 (6.69-7.71) |
| Example 2 | 0.06 | 0.06 (0.12) | 1 | 0.5 | ≤0.03-0.5 (≤0.03-0.5) | 9.56 (8.76-10.4) |
| Example 3 | ≤0.03 (≤0.03) | ≤0.03 (≤0.03) | 8 (16) | 4 (0.5) | n.d. | 7.96 (7.50-8.44) |
| Example 4 | 0.25 (0.25) | 0.06 (0.06) | 4 (1) | 2 (0.5) | ≤0.03-0.12 (≤0.03-0.06) | 4.22 (3.61-4.94) |
| Example 5 | 0.25 (0.25) | 0.5 (1) | 1 (0.5) | 2 (0.5) | ≤0.03-0.12 (≤0.03-0.12) | 6.41 (5.54-7.42) |
| Example 6 | 0.25 (0.12) | ≤0.03 (≤0.03) | 4 (4) | 4 (1) | 1->32 (0.5->32) | 6.46 (5.44-7.67) |
| Example 7 | 0.5 (0.5) | 0.12 (0.5) | 2 (1) | 2 (1) | ≤0.03-0.12 (≤0.03-0.12) | 4.66 (4.40-4.90) |
| Example 8 | 0.12 (0.12) | <0.03 (<0.03) | 0.5 (0.5) | 1 (0.25) | n.d. | 5.64 (5.14-6.19) |

Abbreviations in Table 1:
CI95 LL-UL Confidence interval at 95% probability, lower limit to upper limit
EC *Escherichia coli*
KP *Klebsiella pneumoniae*
AB *Acinetobacter baumannii*
PA *Pseudomonas aeruginosa*
BC *Burkholderia cepacia*
CF Cystic fibrosis
n.d. not determined

EXAMPLES

Herein, including the examples and the reaction scheme the following abbreviations are used:

| | |
|---|---|
| $^1$H-NMR | proton nuclear magnetic resonance spectroscopy |
| ° C. | degrees Celsius |
| BOC | tert-Butyloxycarbonyl |
| BSA | N,O-Bis(trimethylsilyl)-acetamide |
| DMSO | dimethylsulfoxide |
| EDC | N-(3-dimethylaminopropyl)-N'-ethylcarbodiimide hydrochloride |
| eq | equivalents |
| h | hour(s) |
| HOBT | 1-hydroxybenzotriazole |
| HPLC | high performance liquid chromatography |
| MS | mass spectrometry |
| N | normality |
| NMR | nuclear magnetic resonance spectroscopy |
| m/e | mass/charge ratio |
| THF | tetrahydrofuran |

Example 1: (6R,7R)-7-[[(2Z)-2-(2-aminothiazol-4-yl)-2-(1-carboxy-1-methyl-ethoxy)imino-acetyl]amino]-3-[(1,5-dihydroxy-4-oxo-2-pyridyl)methoxy-iminomethyl]-8-oxo-5-thia-1-azabicyclo[4.2.0]oct-2-ene-2-carboxylic acid Scheme 2

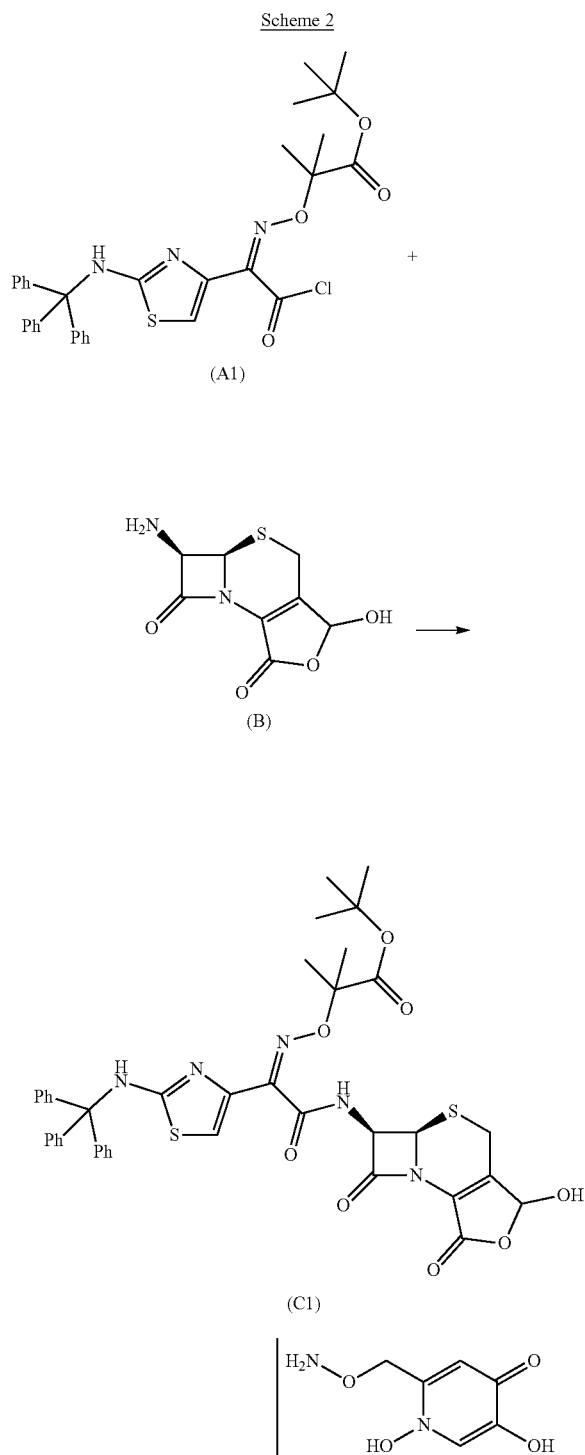

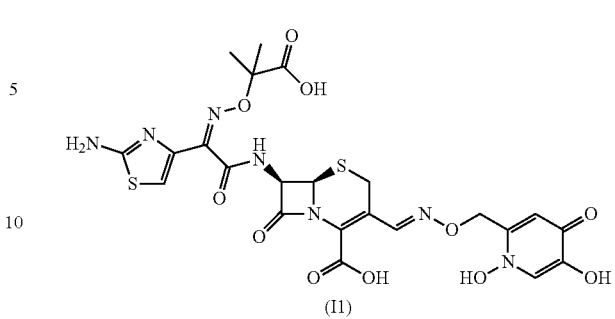

(I1)

Step 1: Amide formation

To an ice cooled solution of compound B (WO95/29182) (1.47 g, 6.44 mmol) and BSA (3.15 mL, 2 eq) in acetonitrile (10 mL) was added a suspension of compound A1 (U.S. Pat. No. 4,500,526) (3.8 g, 1 eq) in acetonitrile (20 mL). The resulting reaction mixture was stirred for 1 h under ice cooling, for 1 h at room temperature and then added slowly to ice water. The resulting precipitate was filtered and dried under reduced pressure to obtain compound C1 as yellow solid which was directly used for the next step. $^1$H-NMR (400 MHz, DMSO-$d_6$, δ, ppm): 9.46 (d, 1H, CONH, J=8.2 Hz), 7.43-7.18 (m, 15H, trityl-H), 6.71 (s, 1H, thiazole-H), 6.30, 6.22 (2×s, 1H, O—CH—O), 5.90 (dd, 1H, H-6, J=5.2 Hz, 8.2 Hz), 5.16 (d, 1H, H-7, J=5.2 Hz), 3.76 (d, 1H, H-2a, J=18.6 Hz), 3.58 (d, 1H, H-2b, J=18.6 Hz), 1.41 (s, 6H, 2×CH$_3$), 1.37 (s, 9H, COO$^t$Bu).

MS m/e: 782 [M+H]$^+$

Step 2: Oxime Formation

To a suspension of compound C1 (Example 1 step 1) and compound D1 (EP0430286) (1.11 g, 1 eq) in acetonitrile (15 mL) was added under ice cooling 1N hydrochloric acid (19.3 mL, 3 eq). The resulting mixture was allowed to warm to room temperature, stirred for 3 h and then slowly added to ice water. The resulting precipitate was filtered off and dried under reduced pressure to obtain compound I1 in protected form as a solid which was directly used for the next step.

$^1$H-NMR (400 MHz, DMSO-$d_6$, 6, ppm): 9.41 (d, 1H, CONH, J=8.1 Hz),), 8.36 (s, 1H, azomethine), 7.80 (s, 1H, dihydropyridine H-6), 7.38-7.17 (m, 15H, trityl-H), 6.74 (s, 11H, dihydropyridine H-3), 6.68 (s, 11H, thiazole-H), 5.79 (dd, 11H, H-6, J=5.0 Hz, 8.1 Hz), 5.23 (d, 1H, H-7, J=5.0 Hz), 5.15 (s, 2H, O—CH$_2$), 3.85 (d, 1H, H-2a, J=18.0 Hz), 3.58 (d, 1H, H-2b, J=18.0 Hz), 1.38 (bs, 6H. 2×CH$_3$), 1.35 (s, 9H, COO$^t$Bu).

MS m/e: 936 [M+H]$^+$

Step 3: Deprotection

Compound I1 in protected form (example I step 2) was dissolved in trifluoracetic acid (20 mL) under ice cooling. The resulting mixture was stirred under ice cooling for 4 h and then slowly added to cold diethyl ether. The resulting precipitate was filtered off and dried under reduced pressure to obtain compound I1 as a solid in the form of a trifluoroacetate salt.

¹H-NMR (400 MHz, MeOH-d₄, δ, ppm): 8.46 (s, 1H, azomethine), 7.84 (s, 1H, dihydropyridine H-6), 6.94 (s, 1H, thiazole-H), 6.84 (s, 1H, dihydropyridine H-3), 5.87 (d, 1H, H-6, J=5.1 Hz), 5.20 (s, 2H, O—CH₂), 5.16 (d, 1H, H-7, J=5.1 Hz), 3.89 (d, 1H, H-2a, J=18.2 Hz), 3.50 (d, 1H, H-2b, J=18.2 Hz), 1.52 (s, 3H, CH₃), 1.51 (s, 3H, CH₃).

MS m/e: 638 [M+H]⁺

Step 4a (optional): Salt Exchange and Chromatography

Compound 11 (1.6 g, 1.85 mmol) in the form of a trifluoroacetate salt (Example 1 Step 3) was suspended in water and a 1N NaOH was slowly added until a pH of 6 to 6.5 was reached. To the resulting solution 1N HCl was added until a pH of 2 was reached and the resulting precipitate was filtered off and subjected to reversed phase chromatography obtain compound I1 after freeze-drying, as an off-white solid in the form of a hydrochloride salt (530 mg).

¹H-NMR (400 MHz, MeOH-d₄, δ, ppm): 8.45 (s, 1H, azomethine), 7.77 (s, 1H, dihydropyridine H-6), 6.81 (s, 1H, thiazole-H), 6.77 (s, 1H, dihydropyridine H-3), 5.87 (d, 1H, H-6, J=5.0), 5.18 (s, 2H, O—CH₂), 5.14 (d, 1H, H-7, J=5.0 Hz), 3.86 (d, 1H, H-2a, J=18.0 Hz), 3.48 (d, 1H, H-2b, J=18.0 Hz), 1.52 (s, 3H, CH₃), 1.50 (s, 3H, CH₃).

MS m/e: 638 [M+H]⁺

The compounds of formula (III) wherein R, X and Z are as defined in Table 2 (Examples 2 to 8) are prepared according, e.g. analogously to a method conventional or as set out under Example 1 Step 2 to 3, and optionally Step 4 above, but using appropriate starting materials.

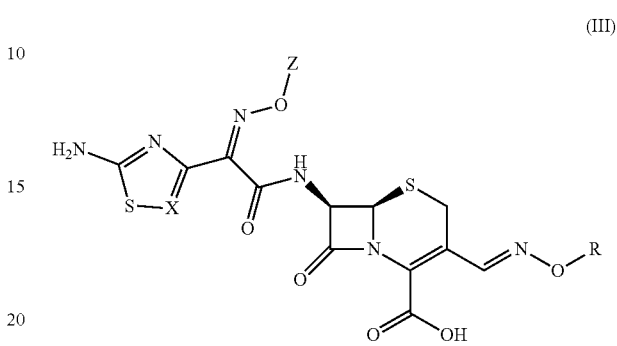

(III)

TABLE 2

| Example | Name/Characterization | R | X | Z |
|---|---|---|---|---|
| 2 | (6R,7R)-7-[[(2Z)-2-(5-amino-1,2,4-thiadiazol-3-yl)-2-(1-carboxy-1-methyl-ethoxy)imino-acetyl]amino]-3-[(1,5-dihydroxy-4-oxo-2-pyridyl)methoxyiminomethyl]-8-oxo-5-thia-1-azabicyclo[4.2.0]oct-2-ene-2-carboxylic acid in the form of a hydrochloride<br>¹H-NMR (400 MHz, MeOH-d₄, δ, ppm): 8.57 (s, 1H, azomethine), 7.92 (s, 1H, dihydropyridine H-6), 6.93 (s, 1H, dihydropyridine H-3), 6.01 (d, 1H, H-6, J = 5.1 Hz), 5.31 (s, 2H, O—CH₂), 5.26 (d, 1H, H-7, J = 5.1 Hz), 4.00 (d, 1H, H-2a, J = 18.2 Hz), 3.60 (d, 1H, H-2b, J = 18.1 Hz), 1.64 (s, 3H, CH₃), 1.63 (s, 3H, CH₃).<br>MS m/e: 639 [M + H]⁺ | (1,5-dihydroxy-4-oxo-2-pyridyl)methyl group structure | N | C(CH₃)₂COOH |
| 3 | (6R,7R)-7-[[(2Z)-2-(5-amino-1,2,4-thiadiazol-3-yl)-2-(fluoromethoxyimino)acetyl]amino]-3-[(1,5-dihydroxy-4-oxo-2-pyridyl)methoxyiminomethyl]-8-oxo-5-thia-1-azabicyclo[4.2.0]oct-2-ene-2-carboxylic acid in the form of a trifluoroacetate<br>¹H-NMR (400 MHz, MeOH-d₄, δ, ppm): 8.56 (s, 1H, azomethine), 8.28 (s, 1H, dihydropyridine H-6), 7.22 (s, 1H, dihydropyridine H-3), 6.00 (d, 1H, H-6, J = 5.1 Hz), 5.82 (d, 2H, O—CH₂—F, J = 54.6 Hz), 5.42 (s, 2H, O—CH₂), 5.28 (d, 1H, H-7, J = 5.1 Hz), 4.00 (d, 1H, H-2a, J = 18.2 Hz), 3.62 (d, 1H, H-2b, J = 18.2 Hz).<br>MS m/e: 583 [M − H]⁻ | (1,5-dihydroxy-4-oxo-2-pyridyl)methyl group structure | N | CH₂F |

TABLE 2-continued

| Example | Name/Characterization | R | X | Z |
|---------|----------------------|---|---|---|
| 4 | 7-[[(2Z)-2-(2-aminothiazol-4-yl)-2-(1-carboxy-1-methyl-ethoxy)imino-acetyl]amino]-3-[2-[(2-chloro-3,4-dihydroxy-benzoyl)amino]ethoxyimino methyl]-8-oxo-5-thia-1-azabicyclo[4.2.0]oct-2-ene-2-carboxylic acid in the form of a hydrochloride<br>$^1$H-NMR (400 MHz, MeOH-d$_4$, δ, ppm): 8.42 (s, 1H, azomethine), 6.92 (s, 1H, thiazole-H), 6.84 (d, 1H, arom. H-6, J = 8.2 Hz), 6.74 (d, 1H, arom. H-5, J = 8.2 Hz), 5.95 (d, 1H, H-6, J = 5.0 Hz), 5.24 (d, 1H, H-7, J = 5.0 Hz), 4.27 (t, 2H, O—CH$_2$, J = 5.4 Hz), 4.03 (d, 1H, H-2a, J = 18.1 Hz), 3.67-3.55 (m, 3H, H-2b, N—CH$_2$), 1.62 (s, 3H, CH$_3$), 1.60 (s, 3H, CH$_3$).<br>MS m/e: 710 [M − H]$^-$ |  | CH | C(CH$_3$)$_2$COOH |
| 5 | 7-[[(2Z)-2-(5-amino-1,2,4-thiadiazol-3-yl)-2-(1-carboxy-1-methyl-ethoxy)imino-acetyl]amino]-3-[2-[(2-chloro-3,4-dihydroxy-benzoyl)amino]ethoxyimino methyl]-8-oxo-5-thia-1-azabicyclo[4.2.0]oct-2-ene-2-carboxylic acid in the form of a hydrochloride<br>$^1$H-NMR (400 MHz, MeOH-d$_4$, δ, ppm): 8.38 (s, 1H, azomethine), 6.83 (d, 1H, arom. H-6, J = 8.3 Hz), 6.74 (d, 1H, arom. H-5, J = 8.3 Hz), 5.91 (d, 1H, H-6, J = 5.0 Hz), 5.20 (d, 1H, H-7, J = 5.0 Hz), 4.24 (t, 2H, O—CH$_2$, J = 5.4 Hz), 3.95 (d, 1H, H-2a, J = 17.9 Hz), 3.61 (t, 2H, N—CH$_2$, J = 5.4 Hz), 3.53 (d, 1H, H-2b, J = 17.9 Hz), 1.63 (s, 3H, CH$_3$), 1.62 (s, 3H, CH$_3$).<br>MS m/e: 713 [M + H]$^+$ |  | N | C(CH$_3$)$_2$COOH |
| 6 | 7-[[(2Z)-2-(5-amino-1,2,4-thiadiazol-3-yl)-2-(fluoromethoxyimino)-acetyl]amino]-3-[2-[(2-chloro-3,4-dihydroxy-benzoyl)amino]ethoxyimino methyl]-8-oxo-5-thia-1-azabicyclo[4.2.0]oct-2-ene-2-carboxylic acid in the form of a hydrochloride<br>$^1$H-NMR (400 MHz, MeOH-d$_4$, δ, ppm): 8.42 (s, 1H, azomethine), 6.85 (d, 1H, arom. H-6, J = 8.2 Hz), 6.76 (m, 1H, arom. H-5, J = 8.2 Hz), 5.95 (d, 1H, H-6, J = 5.0 Hz), 5.81 (d, 2H, O—CH$_2$—F, J = 54.6 Hz), 5.24 (d, 1H, H-7, J = 5.0 Hz), 4.28 (t, 2H, O—CH$_2$, J = 5.4 Hz), 4.03 (d, 1H, H-2a, J = 18.1 Hz), 3.64 (t, 2H, N—CH$_2$, J = 5.4 Hz), 3.59 (d, 1H, H-2b, J = 18.2 Hz).<br>MS m/e: 657 [M − H]$^-$ |  | N | CH$_2$F |

TABLE 2-continued

| Example | Name/Characterization | R | X | Z |
|---------|----------------------|---|---|---|
| 7 | 7-[[(2Z)-2-(2-aminothiazol-4-yl)-2-(1-carboxy-1-methyl-ethoxy)imino-acetyl]amino]-3-[[3-[(2-chloro-3,4-dihydroxy-benzoyl)amino]-trans-cyclobutoxy]iminomethyl]-8-oxo-5-thia-1-azabicyclo[4.2.0]oct-2-ene-2-carboxylic acid in the form of a hydrochloride<br>$^1$H-NMR (400 MHz, MeOH-d$_4$, δ, ppm, characteristic signals): 8.43 (s, 1H, azomethine), 6.89 (s, 1H, thiazole-H), 6.82 (d, 1H, arom. H-6, J = 8.3 Hz), 6.75 (d, 1H, arom. H-5, J = 8.3 Hz), 5.95 (d, 1H, H-6, J = 5.0 Hz), 5.24 (d, 1H, H-7, J = 5.0 Hz), 4.53 (m, 1H, cyclobutane), 4.01 (d, 1H, H-2a, J = 18.0 Hz), 3.61 (d, 1H, H-2b, J = 18.0 Hz), 2.57 (m, 2H, cyclobutane), 2.40 (m, 2H, cyclobutane), 1.62 (s, 3H, CH$_3$), 1.60 (s, 3H, CH$_3$).<br>MS m/e: 738 [M + H]$^+$ | (2-chloro-3,4-dihydroxybenzoyl)amino-trans-cyclobutoxy structure | CH | C(CH$_3$)$_2$COOH |
| 8 | 7-[[(2Z)-2-(2-aminothiazol-4-yl)-2-(1-carboxy-1-methyl-ethoxy)imino-acetyl]amino]-3-{[(3S)-1-(2-chloro-3,4-dihydroxy-benzoyl)pyrrolidine-3-yl]oxyiminomethyl}-8-oxo-5-thia-1-azabicyclo[4.2.0]oct-2-ene-2-carboxylic acid in the form of a hydrochloride<br>$^1$H-NMR (400 MHz, DMSO-d$_6$, δ, ppm, characteristic signals): 8.27 (d, 1H, azomethine), 6.74 (m, 2H, arom. H-6, thiazole-H), 6.58 (dd, 1H, arom. H-5, J = 18.8, 8.4 Hz), 5.84 (m, 1H, H-6), 5.21 (m, 1H, H-7), 4.83-4.71 (2s, 1H, pyrrolidine), 3.90-3.10 (m, 6H, H-2, pyrrolidine), 2.10 (m, 2H, pyrrolidine), 1.44 (m, 6H, CH$_3$).<br>MS m/e: 738 [M + H]$^+$ | (3S)-pyrrolidinyl-(2-chloro-3,4-dihydroxybenzoyl) structure | CH | C(CH$_3$)$_2$COOH |

Appropriate starting materials C2 and C3 (WO98/43981) are prepared according, e.g. analogously, to a method as conventional or according, e.g. analogously as set out in Example 1 Step 1

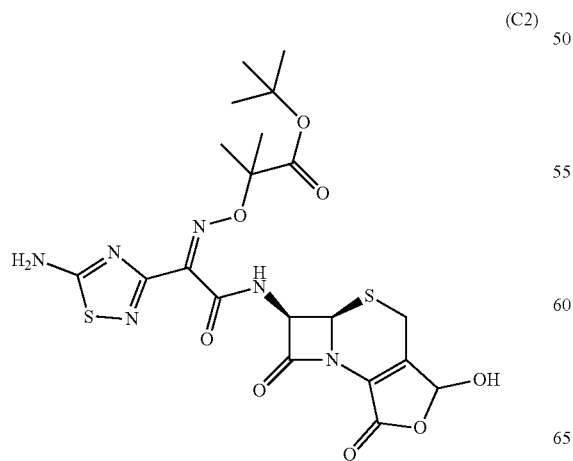

(C2)

(C3)

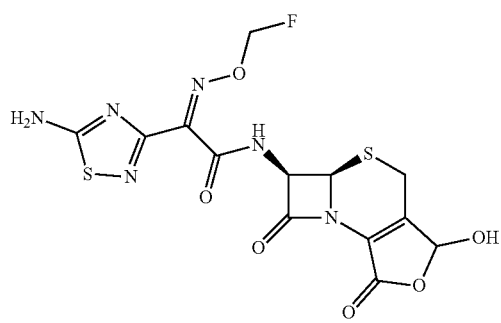

Appropriate starting materials D2, D3 and D4 are prepared according, e.g. analogously, to a method as conventional or as set out below:

Intermediate D2

Scheme 3

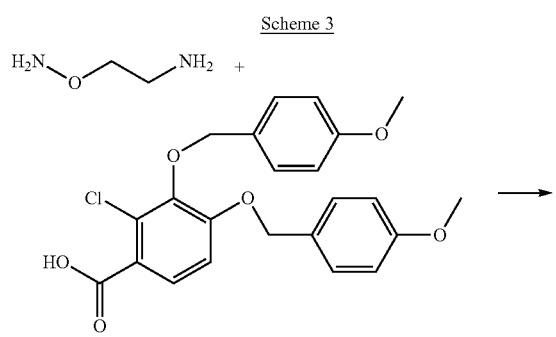

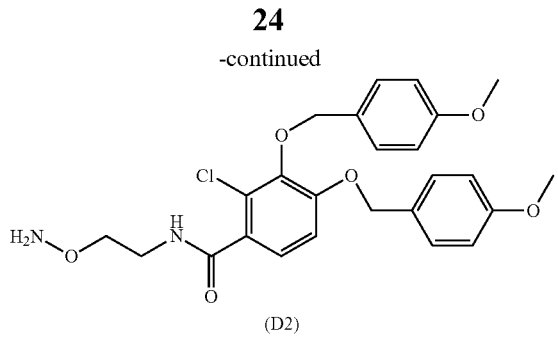

(D2)

To a solution of 2-chloro-3,4-bis[(4-methoxyphenyl)methoxy]benzoic acid (EP 0 416 410) (1 g, 2.33 mmol) in dichloromethane was added HOBT (316 mg, 1 eq), EDC (446 mg, 1 eq) and O-(2-aminoethyl)hydroxylamine hydrochloride (348 mg, 1 eq) and stirred for 1 h at room temperature. Then triethylamine (976 μL, 3eq.) was added and the resulting reaction mixture was stirred at room temperature for further 2 h. The resulting reaction mixture was concentrated to dryness and the residue was purified by chromatography (ethyl acetate/methanol=10/1) to give compound D2 as white solid (1.92 g).

$^1$H-NMR (400 MHz, MeOH-d$_4$, δ, ppm): 7.41 (m, 2H, arom.), 7.30 (m, 2H, arom.), 7.22 (d, 1H, arom., J=8.5 Hz), 7.12 (d, 1H, arom., J=8.5 Hz), 6.96 (m, 2H, arom.), 6.82 (m, 2H, arom.), 5.11 (s, 2H, OCH$_2$), 4.94 (s, 2H, OCH$_2$), 3.83 (s, 3H, OCH$_3$), 3.80 (t, NOCH$_2$, J=5.3 Hz), 3.79 (s, 3H, OCH$_3$), 3.58 (t, 2H, NCH$_2$, J=5.3 Hz).

MS m/e: 487 [M+H]$^+$, 531 [M+HCOO$^-$]

Intermediate D3

Scheme 4

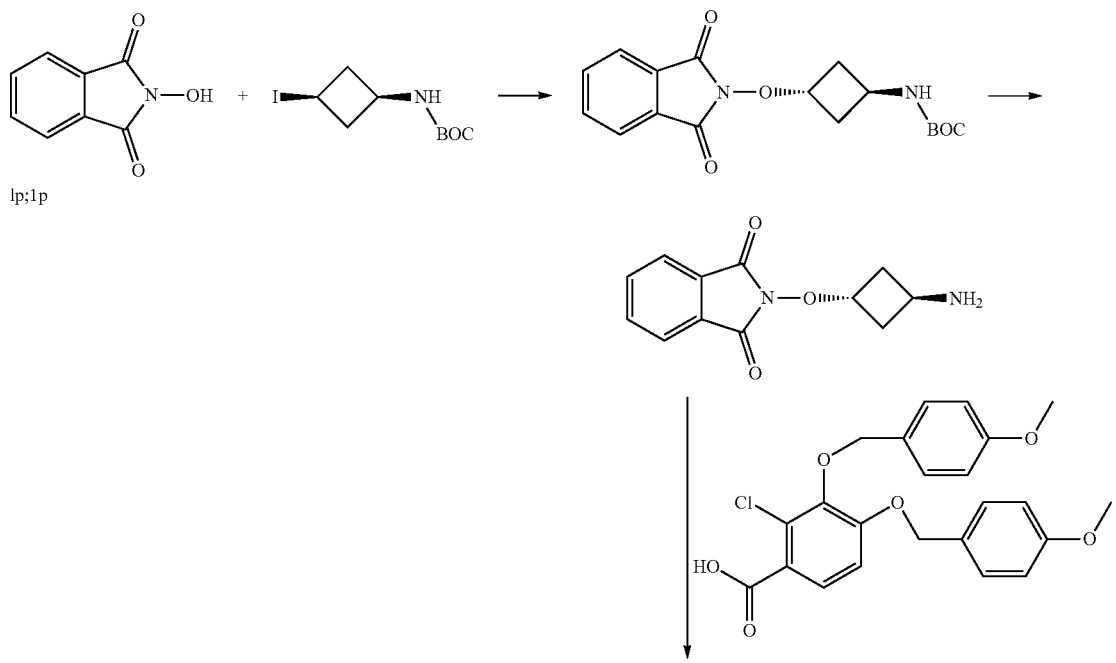

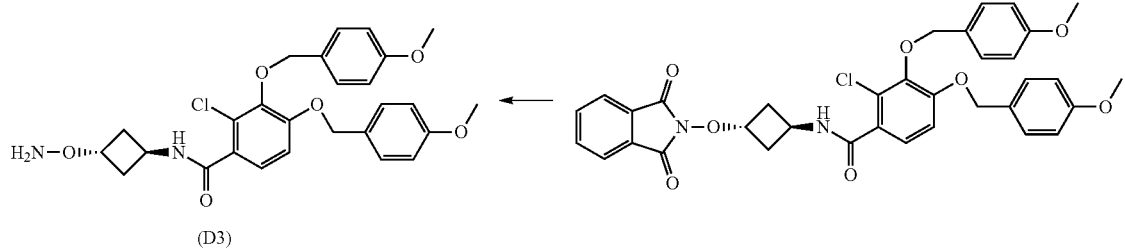

(D3)

Step a

To a solution of N-hydroxy-phthalimide (730 mg, 4.48 mmol) in DMSO was added potassium carbonate (1.55 g, 2.5 eq) and cis-tert-butyl N-(3-iodocyclobutyl)carbamate (1.99 g, 1.5 eq). The resulting reaction mixture was stirred for 3 h at 80° C. and then added slowly to ice water. The resulting precipitate was filtered, dried under reduced pressure and purified by chromatography (dichloromethane/methanol=100/1) to give trans-tert-butyl N-[3-(1,3-dioxoisoindolin-2-yl)oxycyclobutyl]carbamate as white solid (290 mg).

MS m/e: 350 [M+NH$_4^+$]

Step b

To a solution of trans-tert-butyl N-[3-(1,3-dioxoisoindolin-2-yl)oxycyclobutyl]carbamate (2.26 g, 6.80 mmol) in dichloromethane was added hydrogen chloride (2M in diethylether, 12 mL) and stirred at room temperature overnight. The resulting reaction mixture was concentrated to dryness to give trans-2-(3-aminocyclobutoxy)isoindoline-1,3-dione as light-brown solid (1.84 g wet).

MS m/e: 233 [M+H]$^+$

Step c

To a solution of 2-chloro-3,4-bis[(4-methoxyphenyl)methoxy]benzoic acid (EP 0 416 410) (3.40 g, 7.92 mmol) in dichloromethane was added HOBT (1.07 g, 1 eq), EDC (1.52 g, 1 eq) and trans-2-(3-aminocyclobutoxy)isoindoline-1,3-dione as light-brown solid (1.84 g wet, 6.80 mmol) and stirred for 1 h at room temperature. Then triethylamine (3.29 mL, 3eq.) was added and the resulting reaction mixture was stirred at room temperature overnight. The resulting reaction mixture was concentrated to dryness and the residue was purified by chromatography (dichloromethane/methanol/ammonia=100/5/0.5) to give trans-2-chloro-N-[3-(1,3-dioxoisoindolin-2-yl)oxycyclobutyl]-3,4-bis[(4-methoxyphenyl)methoxy]benzamide as a light-yellow solid (2.49 g).

Step d

To a solution of trans-2-chloro-N-[3-(1,3-dioxoisoindolin-2-yl)oxycyclobutyl]-3,4-bis[(4-methoxyphenyl)methoxy]benzamide (1.99 g, 3.09 mmol) in acetonitrile was added hydrazine hydrate (64-65% hydrazine, 0.30 mL, 2 eq) and stirred for 4 h at room temperature. The resulting reaction mixture was filtered. The filtrate was diluted with aqueous ammonium solution and extracted twice with ethyl acetate. The organic phases were combined, dried over Na$_2$SO$_4$, and concentrated to give compound D3 as white solid (0.98 g).

MS m/e: 513 [M+H]$^+$

Intermediate D4

Scheme 5

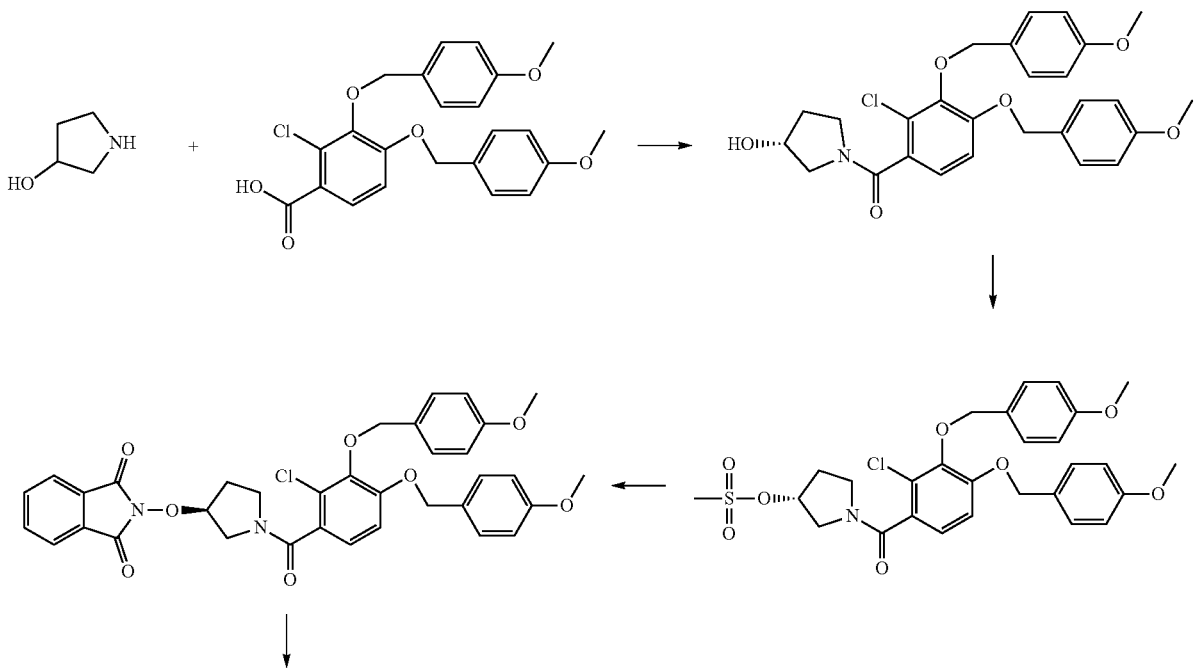

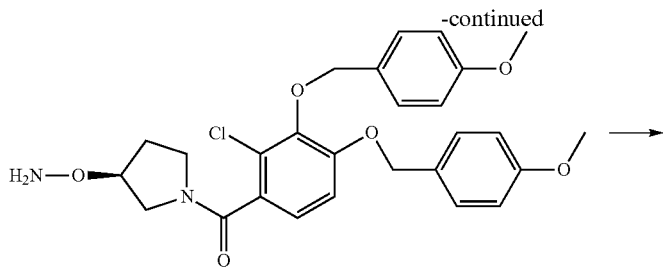
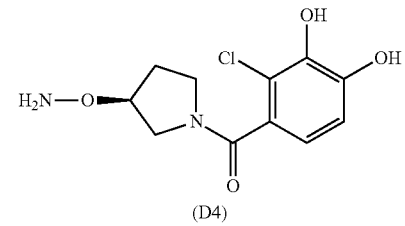

(D4)

Step a

To a solution of (3R)-hydroxypyrrolidine (919 mg, 10.56 mmol) in dichloromethane was added 2-chloro-3,4-bis[(4-methoxyphenyl)methoxy]benzoic acid (EP 0 416 410) (4.53 g, 1 eq), EDC (2.02 g, 1 eq) and HOBT (1.43 g, 1 eq) and stirred at room temperature overnight. The resulting reaction mixture was diluted with dichloromethane and washed with water. The resulting organic phase was concentrated to dryness and purified by chromatography (dichloromethane/methanol/ammonia=100/5/0.5) to give [2-chloro-3,4-bis[(4-methoxyphenyl)methoxy]phenyl]-[(3R)-3-hydroxypyrrolidin-1-yl]methanone (3.93 g).

MS m/e: 498 [M+H]$^+$

Step b

To a solution of [2-chloro-3,4-bis[(4-methoxyphenyl)methoxy]phenyl]-[(3R)-3-hydroxypyrrolidin-1-yl]methanone (3.77 g, 7.57 mmol) in THF was added triethylamine (1.59 mL, 1.5 eq) and methanesulfonyl chloride (0.71 mL, 1.2 eq) under ice cooling and stirred at room temperature for 2 days. The resulting reaction mixture was concentrated, distributed between ethyl acetate and water, and the resulting organic phase washed with saturated aqueous NaCl solution. The organic phase was again separated, dried over Na$_2$SO$_4$, and evaporated to dryness to give crude [(3R)-1-[2-chloro-3,4-bis[(4-methoxyphenyl)methoxy]benzoyl]pyrrolidin-3-yl] methanesulfonate (4.36 g wet).

MS m/e: 573 [M+H]$^+$

Step c

To a solution of crude [(3R)-1-[2-chloro-3,4-bis[(4-methoxyphenyl)methoxy]benzoyl]pyrrolidin-3-yl]methanesulfonate (3.83 g, 6.65 mmol) in DMSO was added potassium carbonate (2.30 g, 2.5 eq) and N-hydroxy-phthalimide (2.00 g, 1 eq) and stirred for 3 h at 80° C. The reaction mixture was distributed between ethyl acetate and water, and the resulting organic phase washed with saturated aqueous NaCl solution. The organic phase was again separated, dried over Na$_2$SO$_4$, and was concentrated to dryness to give crude 2-[(3S)-1-[2-chloro-3,4-bis[(4-methoxyphenyl)methoxy]benzoyl]pyrrolidin-3-yl]oxyisoindoline-1,3-dione (2.73 g wet).

MS m/e: 643 [M+H]$^+$

Step d

To a solution of crude 2-[(3S)-1-[2-chloro-3,4-bis[(4-methoxyphenyl)methoxy]benzoyl]pyrrolidin-3-yl]oxyisoindoline-1,3-dione (2.96 g, 4.60 mmol) in acetonitrile (20 mL) was added hydrazine hydrate (64-65% hydrazine, 0.45 mL, 2 eq) and stirred for 1 h at room temperature. The resulting reaction mixture was diluted with aqueous ammonium solution and extracted twice with ethyl acetate. The organic phases were combined, dried over Na$_2$SO$_4$, and concentrated to give crude [(3S)-3-aminooxypyrrolidin-1-yl]-[2-chloro-3,4-bis[(4-methoxyphenyl)methoxy]phenyl]methanone (1.83 g wet).

MS m/e: 513 [M+H]

Step e

To a solution of crude [(3S)-3-aminooxypyrrolidin-1-yl]-[2-chloro-3,4-bis[(4-methoxyphenyl)methoxy]phenyl]methanone (1.01 g, 1.97 mmol) in dichloromethane (10 mL) was added trifluoroacetic acid (5 mL) and stirred for 1 h at room temperature. The resulting reaction mixture was concentrated and hydrogen chloride (2M in diethylether, 1eq) was added and again evaporated to dryness to give crude (3S)-3-aminooxypyrrolidin-1-yl]-(2-chloro-3,4-dihydroxyphenyl)methanone hydrochloride (1.36 g).

MS m/e: 273 [MH]$^+$

What is claimed is:

1. A compound according to formula (I):

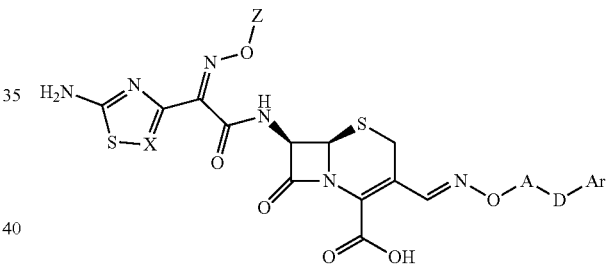

wherein

X is selected from the group consisting of CH, CCl and N,

Z is selected from the group consisting of CH$_2$COOH, CH(CH$_3$)COOH, C(CH$_3$)$_2$COOH and CH$_2$F, D is a single bond connecting A and Ar or selected from the group consisting of CO, NHCO and N(C$_{0-6}$)alkyl-CO, A is selected from the group consisting of a (C$_{1-6}$)alkanediyl and a (C$_{3-6}$)cycloalkanediyl or, if D is N(C$_0$)alkyl-CO, A forms a 4- to 7-membered aliphatic heterocyclic ring with the nitrogen atom of N(C$_0$)alkyl-CO in D, and Ar is a 6-membered aromatic ring with a first hydroxyl group in para-position to D, a second hydroxyl group in meta-position to D, and with at least one electron-withdrawing element.

2. The compound according to claim 1, wherein the electron-withdrawing element may be a heteroatom in the aromatic ring or an electron-withdrawing substituent at the aromatic ring.

3. The compound according to claim 1, wherein the compound is a compound according to formula (II)

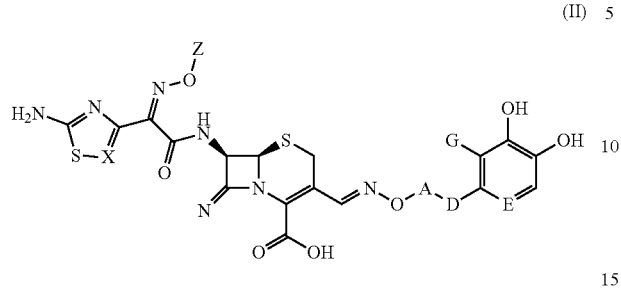

(II)

wherein X, Z, D, and A are defined as in claim 1 and wherein

E is selected from the group consisting of CH, N, $N^+$—$CH_3$, and $N^+$—O—, and G is H or an electron-withdrawing substituent, with the provision that if E is CH, D is selected from the group consisting of CO, NHCO and $N(C_{0-6})$alkyl-CO and G is an electron-withdrawing substituent.

4. The compound according to claim 3, wherein G is an electron-withdrawing substituent selected from the group consisting of F, Cl and $OCF_3$.

5. The compound according to claim 1, wherein a shortest linking path in A is defined by the number of bonds extending between the O of the oxime group and D excluding the bond to the O of the oxime group and excluding the bond to D or the single bond of D, and A is selected such that the shortest linking path in A is shorter than or equal to 3 covalent (C—C) single bonds.

6. The compound according to claim 5, wherein the shortest linking path in A extends over no single (C—C) bond, one cyclic or acyclic (C—C) single bond, or two cyclic covalent (C—C) bonds.

7. The compound according to claim 1, wherein A is selected from the group consisting of methanediyl, ethane-1,2-diyl, propane-1,3-diyl, propane-1,2-diyl, cyclobutane-1,3-diyl, cyclopentane-1,3-diyl, cyclohexane-1,3-diyl, azetidine-1,3-diyl, pyrrolidine-1,3-diyl and piperidine-1,3-diyl, wherein in azetidine-1,3-diyl, pyrrolidine-1,3-diyl and piperidine-1,3-diyl, D is $N(C_0)$alkyl-CO and the nitrogen atom of $N(C_0)$alkyl-CO in D is the nitrogen in the heterocyclic ring.

8. The compound according to claim 3, wherein

D is NHCO or $N(C_{0-6})$alkyl-CO,

A is a $(C_{1-6})$alkanediyl, preferably a $(C_{1-4})$alkanediyl, a $(C_{3-6})$cycloalkanediyl, or A forms a 4- to 7-membered aliphatic heterocyclic ring with the nitrogen atom of $N(C_0)$alkyl-CO in D, E is CH, and G is Cl.

9. The compound according to-claim 3, wherein

D is a single bond,

A is a $(C_{1-6})$alkanediyl, or a $(C_{3-6})$cycloalkanediyl, E is $N^+$—O—, and G is H.

10. The compound according to claim 1, wherein -A-D-Ar is selected from the group consisting of

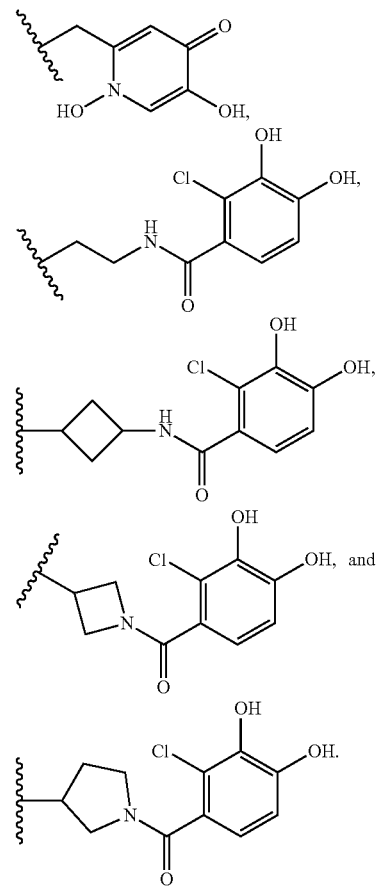

11. The compound according to claim 1, wherein X is CH or N.

12. The compound according to claim 1, wherein Z is $C(CH_3)_2COOH$ or $CH_2F$.

13. The compound according to claim 1, selected from the group consisting of (6R,7R)-7-[[(2Z)-2-(2-aminothiazol-4-yl)-2-(1-carboxy-1-methyl-ethoxy)imino-acetyl]amino]-3-[(1,5-dihydroxy-4-oxo-2-pyridyl)methoxyiminomethyl]-8-oxo-5-thia-1-azabicyclo[4.2.0]oct-2-ene-2-carboxylic acid, (6R,7R)-7-[[(2Z)-2-(5-amino-1,2,4-thiadiazol-3-yl)-2-(1-carboxy-1-methyl-ethoxy)imino-acetyl]amino]-3-[(1,5-dihydroxy-4-oxo-2-pyridyl)methoxyiminomethyl]-8-oxo-5-thia-1-azabicyclo[4.2.0]oct-2-ene-2-carboxylic acid, (6R,7R)-7-[[(2Z)-2-(5-amino-1,2,4-thiadiazol-3-yl)-2-(fluoromethoxyimino)acetyl]amino]-3-[(1,5-dihydroxy-4-oxo-2-pyridyl)methoxyiminomethyl]-8-oxo-5-thia-1-azabicyclo[4.2.0]oct-2-ene-2-carboxylic acid, 7-[[(2Z)-2-(2-aminothiazol-4-yl)-2-(1-carboxy-1-methyl-ethoxy)imino-acetyl]amino]-3-[2-[(2-chloro-3,4-dihydroxy-benzoyl)amino]ethoxyiminomethyl]-8-oxo-5-thia-1-azabicyclo[4.2.0]oct-2-ene-2-carboxylic acid, 7-[[(2Z)-2-(5-amino-1,2,4-thiadiazol-3-yl)-2-(1-carboxy-1-methyl-ethoxy)imino-acetyl]amino]-3-[2-[(2-chloro-3,4-dihydroxy-benzoyl)amino]ethoxyiminomethyl]-8-oxo-5-thia-1-azabicyclo[4.2.0]oct-2-ene-2-carboxylic acid, 7-[[(2Z)-2-(5-amino-1,2,4-thiadiazol-3-yl)-2-(fluoromethoxyimino)-acetyl]amino]-3-[2-[(2-chloro-3,4-dihydroxy-benzoyl)amino]ethoxyiminomethyl]-8-oxo-5-thia-1-azabicyclo[4.2.0]oct-2-ene-2-carboxylic acid, 7-[[(2Z)-2-(2-aminothiazol-4-yl)-2-(1-carboxy-1-methylethoxy)imino-acetyl]amino]-3-1[[3-[(2-chloro-3,4-dihydroxy-benzoyl)amino]-trans-cyclobutoxy]iminomethyl]-8-oxo-5-thia-1-azabicyclo[4.2.0]oct-2-ene-2-carboxylic acid and 7-[[(2Z)-2-(2-aminothiazol-4-yl)-2-(1-carboxy-1-methylethoxy)imino-acetyl]amino]-3-{[(3S)-1-(2-chloro-3,4-dihydroxy-benzoyl)pyrrolidine-3-yl]oxyiminomethyl}-8-oxo-5-thia-1-azabicyclo[4.2.0]oct-2-ene-2-carboxylic acid.

14. A composition comprising a compound of claim 1 in association with at least one pharmaceutical excipient, optionally comprising further at least one pharmaceutical active agent.

15. A method of treating a bacterial infection in a subject in need thereof, comprising administering an effective amount of a compound according to formula (I)

to the subject, wherein

X is selected from the group consisting of CH, CCl and N,

Z is selected from the group consisting of $CH_2COOH$, $CH(CH_3)COOH$, $C(CH_3)_2COOH$ and $CH_2F$, D is a single bond connecting A and Ar or selected from the group consisting of CO, NHCO and $N(C_{0-6})$alkyl-CO, A is selected from the group consisting of a $(C_{1-6})$alkanediyl and a $(C_{3-6})$cycloalkanediyl or, if D is $N(C_0)$alkyl-CO, A forms a 4- to 7-membered aliphatic heterocyclic ring with the nitrogen atom of $N(C_0)$alkyl-CO in D, and Ar is a 6-membered aromatic ring with a first hydroxyl group in para-position to D, a second hydroxyl group in meta-position to D, and with at least one electron-withdrawing element, and wherein the subject has the bacterial infection.

16. The method according to claim 15, wherein the bacterial infection is mediated by Gram-negative bacteria.

17. The method according to claim 15, wherein the bacterial infection is selected from the group consisting of a respiratory tract infection of the lower and/or upper respiratory tract, an urinary tract infection, an intraabdominal infection, a systemic infection, a prosthetic joint infection, a gastrointestinal infection, and an infection of skin and/or soft tissue.

18. The method according to claim 15, wherein the bacterial infection is mediated by a bacteria selected from the group consisting of *Escherichia coli*, *Salmonella typhimurium*, *Citrobacter freundii*, *Klebsiella pneumoniae*, *Enterobacter cloacae*, *Enterobacter aerogenes*, *Moraxella catarrhalis*, *Proteus mirabilis*, *Proteus vulgaris*, *Providencia stuartii*, *Serratia marcescens*, *Acinetobacter baumannii*, *Acinetobacter lwoffi*, *Pseudomonas aeruginosa*, *Haemophilus influenzae*, *Burkholderia cepacia*, *Burkholderia cenocepatia*, *Burkholderia vietnamensis*, *Streptococcus* spp., and *Streptococcus pneumoniae*.

19. The method according to claim 15, wherein the effective amount of the compound according to formula (I) is administered in the form of a pharmaceutical composition.

20. The compound according to claim 5, wherein

A is selected such that the shortest linking path in A is shorter than or equal to 2 covalent (C—C) single bonds.

21. The compound according to claim 5, wherein

A is selected such that the shortest linking path in A is shorter than 2 acyclic covalent (C—C) single bonds.

22. The compound according to claim 7, wherein A is selected from from methanediyl, ethane-1,2-diyl, cyclobutane-1,3-diyl, and pyrrolidine-1,3-diyl with D being $N(C_0)$alkyl-CO and the nitrogen atom of $N(C_0)$alkyl-CO in D being the nitrogen in the pyrrolidine ring.

23. The compound according to claim 8, wherein A is a $(C_2)$alkanediyl ethane-1,2-diyl, or a $(C_{4-5})$cycloalkanediyl, or A forms a 5-membered aliphatic heterocyclic ring.

24. The compound according to claim 23, wherein A is a $(C_4)$cycloalkanediyl cyclobutane-1,3-diyl, or A forms a 5-membered heterocyclic ring pyrrolidine-1,3-diyl with the nitrogen atom of $N(C_0)$alkyl-CO in D being the nitrogen in the pyrrolidine.

25. The compound according to claim 9, wherein A is a $(C_{1-4})$alkanediyl.

26. The compound according to claim 25, wherein

A is methanediyl.

27. The compound according to claim 10, wherein

-A-D-Ar is selected from the group consisting of

33

-continued

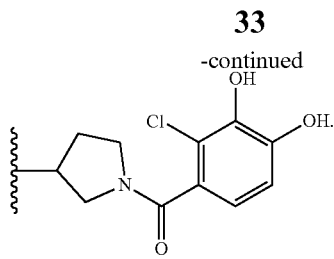

28. The compound according to claim 27, wherein
-A-D-Ar
is selected from the group consisting of

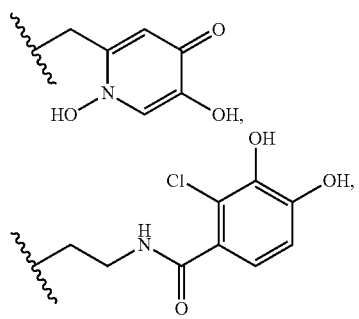

34

-continued

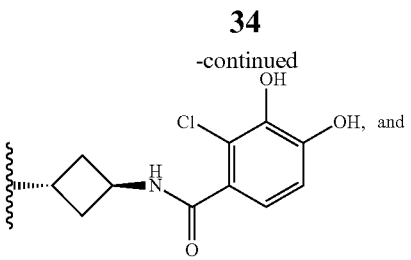

29. The method according to claim 17, wherein the subject having the upper and/or lower respiratory tract infection has cystic fibrosis and/or bronchiectasis.

30. The method according to claim 18, wherein the bacteria selected from the group consisting of *Escherichia coli, Klebsiella pneumoniae, Acinetobacter baumannii, Pseudomonas aeruginosa,* and *Burkholderia cepacia.*

* * * * *